US010098848B2

(12) United States Patent
Price

(10) Patent No.: US 10,098,848 B2
(45) Date of Patent: Oct. 16, 2018

(54) INOSITOL-CONTAINING COMESTIBLE UNITS AND METHODS OF TREATMENT USING THE SAME

(71) Applicant: Richard Louis Price, Suffern, NY (US)

(72) Inventor: Richard Louis Price, Suffern, NY (US)

( * ) Notice: Subject to any disclaimer, the term of this patent is extended or adjusted under 35 U.S.C. 154(b) by 0 days.

(21) Appl. No.: 15/346,079

(22) Filed: Nov. 8, 2016

(65) Prior Publication Data

US 2017/0049715 A1    Feb. 23, 2017

Related U.S. Application Data

(63) Continuation-in-part of application No. 14/596,726, filed on Jan. 14, 2015, which is a continuation-in-part of application No. 14/245,121, filed on Apr. 4, 2014, now Pat. No. 9,603,812, which is a continuation-in-part of application No. 14/166,483, filed on Jan. 28, 2014, which is a continuation-in-part of application No. 13/860,824, filed on Apr. 11, 2013, now Pat. No. 9,211,284.

(51) Int. Cl.

| *A61K 31/047* | (2006.01) |
| *A61K 9/00* | (2006.01) |
| *A21D 2/18* | (2006.01) |
| *A21D 13/08* | (2006.01) |
| *A23L 33/125* | (2016.01) |
| *A61K 31/165* | (2006.01) |
| *A61K 31/4168* | (2006.01) |

(52) U.S. Cl.
CPC ............ *A61K 31/047* (2013.01); *A21D 2/181* (2013.01); *A21D 13/08* (2013.01); *A23L 33/125* (2016.08); *A61K 9/0056* (2013.01); *A61K 31/165* (2013.01); *A61K 31/4168* (2013.01); *A23V 2002/00* (2013.01)

(58) Field of Classification Search
CPC ..... A23L 33/125; A21D 2/181; A61K 9/0056; A61K 31/047; A61K 31/4168; A61K 31/165; A23V 2002/00
See application file for complete search history.

(56) References Cited

U.S. PATENT DOCUMENTS

| 3,454,701 A | 7/1969 | Zeile et al. |
| 5,854,290 A | 12/1998 | Arnsten et al. |
| 5,869,100 A | 2/1999 | Horacek |
| 6,287,599 B1 | 9/2001 | Burnside et al. |
| 6,811,794 B2 | 11/2004 | Burnside et al. |
| 8,062,667 B2 | 11/2011 | Mehta et al. |
| 8,287,903 B2 | 10/2012 | Mehta et al. |
| 8,455,548 B2 | 6/2013 | Luhrs et al. |
| 8,557,792 B2 | 10/2013 | Castelli et al. |
| 2004/0175442 A1 | 9/2004 | Gardiner et al. |
| 2005/0058759 A1 | 3/2005 | Schmidt |

FOREIGN PATENT DOCUMENTS

WO    WO 2009/023975    *   2/2009   ............. C07J 17/00

OTHER PUBLICATIONS

Smitten Kitchen (https://smittenkitchen.com/2008/01/chocolate-chip-cookies/, accessed Oct. 16, 2017, published Jan. 14, 2008) (Year: 2008).*
Yale University, "Guanfacine for the Treatment of Hyperactivity in Pervasive Developmental Disorder", https://clinicaltrials.gov/ct2/show/study!NCT01238575?term=intuniv+hyperactivity+in+au, Aug. 19, 2014.
Levine, J., et al. "Inositol Treatment of Autism", J Neural Transm (1997) 04: 307-310.
Blankenship, K., et al., "Guanfacine Extended Release in Two Patients with Pervasive Developmental Disorders", Journal of Child and Adolescent Psycopharmacology, vol. 21, No. 3, 2011.
Ming, X., et al., "Use of Clonidine in Children With Autism Spectrum Sisorders", Brain & Development 30 (2008) 454-460.
International Search Report and Written Opinion for PCT Application PCT/US2014/032933 dated Aug. 7, 2014.
Woeller, K., "Natural Remedy Support for Obsessive Compulsive Disorder in Autism-Spectrum Children", http://drkurtwoeller.blogspot.com/2008/12/natural-remedy-support-for-obsessive.html, Dec. 12, 2008.
Autism Speaks, "What Are the Symptoms of Autism?", https://www.autismspeaks.org/what-autism/symptoms, May 10, 2016.
U.S. Food and Drug Administration, "Beware of False or Misleading Claims for Treating Autism", http://www.fda.gov/forconsumers/consumerupdates/ucm394757.htm, Apr. 25, 2014.
Pscyh Central, "Medications for Autism", http://psychcentral.com/lib/medications-for-autism/, May 17, 2016.

* cited by examiner

*Primary Examiner* — Angela C Brown-Pettigrew
(74) *Attorney, Agent, or Firm* — David B. Gornish; Eckert Seamans Cherin & Mellott LLC

(57) ABSTRACT

A method for treating a patient having one or more of anxiety, hypersensitivity, restricted areas of interest, repetitive behaviors, irritability and emotional lability, or otherwise requiring a calming effect, is disclosed. The method includes administering to the patient a plurality of comestible units, e.g., cookies, cumulatively comprising a therapeutically effective amount of inositol.

17 Claims, No Drawings

INOSITOL-CONTAINING COMESTIBLE UNITS AND METHODS OF TREATMENT USING THE SAME

CROSS-REFERENCE TO RELATED APPLICATIONS

This application is a continuation-in-part of U.S. patent application Ser. No. 14/596,726, entitled "Inositol-Containing Comestible Units and Methods of Treating Autistic Spectrum Disorder Using the Same," filed Jan. 14, 2015 and currently pending, which is a continuation-in-part of U.S. patent application Ser. No. 14/245,121, entitled "Treatment of Autistic Spectrum Disorder, filed Apr. 4, 2014, which is a continuation-in-part of U.S. patent application Ser. No. 14/166,483, entitled "Diagnosis and Treatment of a Form of Autistic Spectrum Disorder, filed Jan. 28, 2014, which is a continuation-in-part of U.S. patent application Ser. No. 13/860,824, entitled "Diagnosis and Treatment of P.R.I.C.E. Syndrome," filed Apr. 11, 2013 (now U.S. Pat. No. 9,211,284), all of which are incorporated by reference herein in their entireties.

BACKGROUND OF THE INVENTION

1. Field of Invention

The invention relates to treatment of psychiatric or neurological symptoms that may or may not relate to an underlying psychiatric disorder recognized in the DSM 5.0, e.g., Autistic Spectrum Disorder, Anxiety, Obsessive-Compulsive Disorder. More particularly, the invention relates to administering to a person having one or more symptoms whether or not related to an underlying psychiatric and/or neurological condition) that respond to therapeutic doses of inositol provided in a plurality of comestible units, e.g., cookies. Such symptoms may include, among others, anxiety, hypersensitivity, restricted areas of interest, repetitive behaviors, irritability and emotional lability.

2. Description of Related Art

When a psychiatrist is presented with a patient exhibiting one or more behaviors such as poor social skills, defiance, lack of patience, difficulty paying attention, ritualistic behavior and/or mood swings, where such behavior(s) interferes with normal functioning, the psychiatrist must first make a diagnosis before formulating a treatment plan.

Today, the psychiatrist's nomenclature, i.e., the criteria for psychiatric evaluation and classification is provided in the Diagnostic and Statistical Manual of Mental Disorders ("DSM"), a periodically revised psychiatric "Bible" published by the American Psychiatric Association. The current version of the DSM is DSM 5.0, which was published on May 18, 2013.

The psychiatrist's professional judgment in rendering a diagnosis is largely informed by the criteria for various disorders set forth in the DSM. Thus, a psychiatrist presented with a patient exhibiting any such symptoms as those described above would consult the DSM in rendering a diagnosis. The diagnosis would, in turn, inform a treatment program. Whether a given patient is determined, for example, to have AMID as opposed to Hypomania in Bipolar Disorder, depends on whether the patient's symptoms comport with criteria set forth for these conditions in the DSM. Proper diagnosis is critical since a wrong diagnosis will likely lead to an ineffective or even potentially harmful treatment program.

The DSM 5.0 definition of Autism Spectrum Disorder ("ASD") is as follows:

A. Persistent deficits in social communication and social interaction across contexts, not accounted for by general developmental delays, and manifest by all 3 of the following:
 1. Deficits in social-emotional reciprocity: ranging from abnormal social approach and failure of normal back and forth conversation through reduced sharing of interests, emotions, and affects and response to total lack of initiation of social interaction.
 2. Deficits in nonverbal communicative behaviors used for social interaction: ranging from poorly integrated verbal and nonverbal communication, through abnormalities in eye contact and body language, or deficits in understanding and use of nonverbal communication, to total lack of facial expression or gestures.
 3. Deficits in developing and maintaining relationships appropriate to developmental level (beyond those of caregivers); ranging from difficulties to adjusting behavior to suit different social contexts through difficulties in sharing imaginative play and in making friends to an apparent absence of interest in people.
B. Restricted, repetitive patterns of behavior, interests, or activities as manifested by at least two of the following:
 1. Stereotyped or repetitive speech, motor movements, or use of objects such as simple motor stereotypes, echolalia, repetitive use of objects, or idiosyncratic phrases).
 2. Excessive adherence to routines, ritualized patterns of verbal or nonverbal behavior, or excessive resistance to change such as motoric rituals, insistence on same route or food, repetitive questioning or extreme distress at small changes).
 3. Highly restricted, fixated interests that are abnormal in intensity or focus (such as strong attachment to or preoccupation with unusual objects, excessively circumscribed or perseverative interests).
 4. Hyper- or hypo-reactivity to sensory input or unusual interest in sensory aspects of environment (such as apparent indifference to pain/heat/cold, adverse response to specific sounds or textures, excessive smelling or touching of objects, fascination with lights or spinning objects).
C. Symptoms must be present in early childhood (but may not become fully manifest until social demands exceed limited capacities).
D. Symptoms together limit and impair everyday functioning.

Part A of the DSM 5.0 definition of ASD and Part B of the DSM 5.0 definition of ASD are hereinafter collectively referred to as "core symptoms" of ASD or "core ASD symptoms," since they are, by definition, present in all ASD patients. Throughout this specification, the constituent symptoms of the core symptoms of ASD may be individually referred to respectively as "part A of the DSM 5.0 definition of ASD" and "part B of the DSM 5.0 definition of ASD."

Other symptoms that may be manifest in ASD patients and which are associated with their ASD are referred to herein as "associated symptoms" of ASD or "associated ASD symptoms". Such associated symptoms of ASD may include at least one of the following: impulsivity, concentration deficit or attention deficit and emotional lability/irritability. As discussed below, as relates to an optional aspect of the invention, emotional lability/irritability may also manifest itself in patients with a different underlying condition or with no particular diagnosed underlying condition.

The term "impulsivity," as used herein, is characterized by the following: often blurts out answers before questions have been completed and/or often has difficulty waiting for his/her turn and/or often interrupts or intrudes on others (e.g., butts into conversations or games).

The terms "concentration deficit" and "attention deficit" are synonymous with each other and are therefore interchangeable. As used herein, the terms "concentration deficit" and "attention deficit" are characterized by the following: deficits in concentration as evidenced by often having difficulty sustaining attention in tasks or play activities, often does not seem to listen when spoken to directly, is often easily distracted by extraneous stimuli.

The terms "emotional lability" and "irritability," are synonymous with each other and are therefore interchangeable. As used herein, "emotional lability" and "irritability" are compounded into the single term (which is synonymous with each individual term): "emotional lability/irritability." Emotional lability/irritability is characterized by the following: severe, reactive mood swings in response to real or perceived situations where demanded needs are not being met in the environment. Emotional lability/irritability may optionally be measured using the Aberrant Behavior Checklist irritability subscale.

The Applicant has discovered a pervasive subpopulation within ASD that responds particularly well to a combination therapy that the Applicant has invented. In addition to the core symptoms of DSM 5.0 ASD, defined above, the Applicant has found patients in this subpopulation have one or more (usually all) associated symptoms of ASD, as defined above (i.e., impulsivity, concentration deficit or attention deficit and/or emotional lability/irritability). The combination therapy to treat ASD that Applicant invented, namely administering a therapeutically effective amount of an alpha-2 adrenergic agonist in an extended release dosage form in combination with a therapeutically effective amount of inositol, is described in detail in the following of Applicant's patent applications, all of which are incorporated by reference herein in their entireties: WO 2014/168820 and U.S. Pat. Pub. Nos. 2014/0309271, 2014/0309270 and 2014/0309269.

Based on Applicant's experience and insights, the aforementioned combination therapy is a superior treatment for ASD compared to use of either agent alone. For example, neither agent alone is effective in treating all core symptoms of ASD and associated symptoms of ASD, whereas the combination is effective in treating all such symptoms. Moreover, Applicant has found that the combination exhibits a synergistic effect in treating Part A of the DSM 5.0 definition of ASD and emotional lability/irritability.

Notwithstanding the superior efficacy of the combination over administration of either agent alone in ASD, monotherapy with only one of these agents is still far more effective than either doing nothing or administering other known drugs. Applicant has seen cases in which ASD patients were misdiagnosed based on patients' presenting associated symptoms of ASD, which treating physicians misinterpreted as being indicative of underlying conditions unrelated to ASD. Such misdiagnoses led to prescribing drugs that either did not help, or exacerbated these patients' symptoms, and/or caused serious side effects. Such drugs included psychostimulants, Strattera, Wellbutrin, Provigil, Nuvigil, Tenex, propranonol, selective serotonin re-uptake inhibitors, serotonin and norepinephrine reuptake inhibitors, mood stabilizers and atypical antipsychotics. See, e.g., Examples 1 and 2 of Applicant's U.S. Pat. Pub. 2014/0309270.

Whereas the aforementioned drugs were found to be ineffective or harmful to ASD patients, Applicant has found that an extended release alpha-2 adrenergic agonist, such as extended release clonidine (e.g., marketed as KAPVAY®) or extended release guanfacine (e.g., marketed as INTUNIV®) as monotherapy for ASD is effective in treating some ASD symptoms. Likewise, Applicant has found that high doses of inositol are effective as a monotherapy in treating some ASD symptoms. While Applicant's combination therapy is superior and preferred for treating ASD over monotherapy using either agent alone, such monotherapy is still an improvement over anything else known to Applicant (aside of course from Applicant's combination therapy). Given the urgency of the health need for effective ASD treatment, and the fact that regulatory approval of any new drug (in this case, the combination therapy) generally takes years, there is a need for a readily available treatment for ASD patients.

Inositol is a natural supplement that is already widely available, e.g., in vitamin stores, without a prescription. Applicant has discovered that high doses of inositol are safe and effective in treating Part B of the DSM 5.0 definition of ASD and the associated symptom of ASD of emotional lability/irritability. Alleviation of these symptoms alone would provide some relief to ASD patients and their caretakers. While there are exceptions, Applicant has found that therapeutic doses of inositol for ASD patients tend to be about 9,000 mg to about 32,400 mg per day, more typically about 18,000 mg to about 32,400 mg per day. Inositol is typically available as a supplement, e.g., in powder form. Given the large amounts of inositol generally necessary to provide therapeutic doses to ASD patients, such commercially available inositol is not typically administered orally without being mixed with some other substance. For example, inositol is typically mixed into a drink or semi solid food, e.g., applesauce.

However, Applicant has found that children sometimes do not respond well to taking large doses of inositol mixed in a drink. Large amounts of inositol, e.g., 9,000 mg to 32,400 mg per day, may be difficult for parents to premeasure with precision and to carry in the standard large bottles that contain the inositol powder when the child is not home. Some may opt to carry premeasured doses of inositol in, e.g., sandwich bags or the like, when on the go. However, this may appear suspicious, since the powder has the visual appearance of cocaine. Moreover, children also may refuse to finish the drink or food into which the inositol is mixed or refuse to eat/drink the mixture altogether when the child realizes that he/she is consuming medication. The bottom line is that pharmacotherapy is not effective if it cannot be administered and inositol in its typical commercial form can be problematic in this regard.

There is thus a need for an improved method for delivering high doses of inositol to a patient in need thereof. This need extends to any such patients, whether suffering from a DSM 5.0 recognized psychiatric condition (e.g., ASD) or not. For example, whether or not symptomology is rooted in ASD, a different condition, or no recognized or diagnosed underlying condition, there is a need for an improved method for delivering high doses of inositol in patients exhibiting one or more of the following symptoms: anxiety, hypersensitivity, restricted areas of interest, repetitive behaviors, irritability and emotional lability.

BRIEF SUMMARY OF THE INVENTION

Accordingly, in one aspect, the present invention is directed to a method for treating a patient having ASD. As used herein, the term ASD is defined as the diagnostic criteria for DSM 5.0 as published by the American Psychiatric Association. The method includes administering to the patient a therapeutically effective amount of inositol, preferably in a plurality of comestible units, e.g., baked goods such as cookies. A therapeutically effective amount of inositol is an amount that will reduce one or more core symptoms of ASD or associated ASD symptoms. Thus, in one aspect, the method includes administering to the ASD patient a plurality of comestible units, e.g., cookies, cumulatively comprising a therapeutically effective amount of inositol. Optionally, the plurality of comestible units comprising inositol may be administered to a patient having ASD in combination with a therapeutically effective amount of an alpha-2 adrenergic agonist in an extended release dosage form.

In another aspect, the present invention is directed to a method for reducing, to a clinically meaningful degree, one or more symptoms associated with ASD in a patient having ASD. The method includes administering to the patient a maximum effective dose of inositol. The maximum effective dose of inositol is determined by providing an amount of inositol to the patient that induces diarrhea and then titrating down to a lower dose that does not induce diarrhea but is immediately below a dose which does induce diarrhea. As used herein in the foregoing context, the term "immediately below" means less than an amount which induces diarrhea, although not substantially less that amount. For example, "immediately below" may mean within 10% of the amount of inositol that induces diarrhea in the patient. The maximum effective dose according to this method is the lower dose.

In another aspect, the present invention is directed to a method for reducing, to a clinically meaningful degree, one or more symptoms associated with ASD in a patient having ASD, e.g., part B of the DSM 5.0 definition of ASD and/or emotional lability/irritability. The method comprises administering to the patient a therapeutically effective amount of inositol, wherein the therapeutically effective amount of inositol is from about 9,000 mg to about 32,400 mg per day. This may be achieved, e.g., through administering a plurality of comestible units, each comprising a predetermined amount of inositol.

In another aspect, the present invention is directed to a method for treating a patient having one or more of the following symptoms, irrespective of whether such symptoms are rooted in an underlying psychiatric disorder or a neurological disorder: anxiety, hypersensitivity, restricted areas of interest, repetitive behaviors, irritability and emotional lability. The method includes administering to the patient a therapeutically effective amount of inositol, preferably in a plurality of comestible units, e.g., baked goods such as cookies. A therapeutically effective amount of inositol, in the context of this aspect of the invention is an amount that will reduce one or more of the aforementioned symptoms. Such therapeutically effective amount of inositol may be from about 9,000 mg to about 32,400 mg per day. Thus, in one aspect, the method includes administering a plurality of comestible units, e.g., cookies, cumulatively comprising a therapeutically effective amount of inositol, to a patient having one or more of: anxiety, hypersensitivity, restricted areas of interest, repetitive behaviors, irritability and emotional lability.

In another aspect, the present invention is directed to a method for treating a patient in need of a calming effect. The method includes administering to the patient a therapeutically effective amount of inositol, preferably in a plurality of comestible units, e.g., baked goods such as cookies. Such therapeutically effective amount of inositol may be from about 9,000 mg to about 32,400 mg per day.

Optionally, in any embodiment, the selected method provides a therapeutic effect on the patient after two weeks of consistent practicing of the method on the patient.

Optionally, in any embodiment, inositol provides a sweetening effect to the comestible unit, functioning as a sugar substitute in addition to providing a therapeutic effect.

Optionally, in any embodiment, the inositol-containing comestible units are baked goods.

Optionally, in any embodiment, the inositol-containing comestible units are prepared in a cooking or baking process wherein the units are heated in an oven environment that is set at least 300° F. or higher for at least eight minutes.

Optionally, the therapeutically effective amount of inositol is from 18,000 mg to 32,400 mg per day, the plurality of inositol-containing comestible units are cookies, wherein each cookie contains from 2,500 to 4,500 mg of inositol and two to four cookies are administered to the patient two or three times daily.

Optionally, in any embodiment, the inositol in the plurality of inositol-containing comestible units does not have reduced efficacy in treating the patient due to the inositol being exposed to high temperatures during a cooking or baking process, compared to an identical dose of inositol administered in raw powder form.

Optionally, the inositol-containing comestible units are gummies, candies or lozenges.

DETAILED DESCRIPTION OF THE INVENTION

Whether administered as a monotherapy for ASD or in combination with an extended released alpha-2 adrenergic agonist, or for the treatment of other symptoms (which may or may not be rooted in ASD or another underlying psychiatric or neurological disorder), inositol according to the present invention is preferably administered via comestible units, as described below.

As used herein, the phrase "greater efficacy in reducing" with respect to one or more symptoms, means that based on a psychiatrist's qualitative evaluation using ordinary skill and/or evaluation using a recognized quantitative scale in the field of psychiatry, optionally the Social Responsiveness Scale ("SRS," explained more fully below), the improvement in the one or more symptoms is greater, and preferably unexpectedly greater using the inositol-containing comestible, than a placebo (e.g., placebo comestible).

The phrase "to a clinically meaningful degree" as used herein means noticeable reduction in a given symptom based on a psychiatrist's qualitative evaluation using ordinary skill and/or evaluation using a recognized quantitative scale in the field of psychiatry, optionally the SRS. The method includes reducing, to a clinically meaningful degree, part B of the DSM 5.0 definition of ASD and/or emotional lability/irritability in a patient having ASD. In another aspect, the method includes reducing, to a clinically meaningful degree, one or more of the following symptoms, irrespective of whether such symptoms stem from a DSM-recognized psychiatric disorder or neurological disorder: anxiety, hypersensitivity, restricted areas of interest, repetitive behaviors, irritability and emotional lability. In another aspect, the method includes providing, to a clinically meaningful degree, a calming effect to a patient in need thereof (whether or not the patient suffers from a DSM-recognized psychiatric disorder or neurological disorder).

In any embodiment, the method comprises administering a plurality of inositol-containing comestible units, wherein the plurality of inositol-containing comestible units each comprises a predetermined amount of inositol. Optional inositol dosing per comestible unit is described below.

Inositol Chemistry and Dosing in ASD

Inositol or cyclohexane-1,2,3,4,5,6-hexol is a chemical compound with formula $C_6H_{12}O_6$ or $(-CHOH-)_6$, a six-fold alcohol (polyol) of cyclohexane. Inositol exists in nine possible stereoisomers. The most prominent form, widely occurring in nature, is cis-1,2,3,5-trans-4,6-cyclohexanehexol, or myo-inositol (former name meso-inositol). Inositol has been shown to have a taste that is half the sweetness of table sugar. For this reason, the Applicant has found the taste of inositol to be well tolerated by ASD patients or other children who are very particular and who thus do not respond favorably to medications with strong tastes or smells.

In addition, Applicant has found that inositol, in high amounts (as disclosed herein) can also serve as a sugar substitute in comestible units, e.g., cookies. In this way, the inositol serves a dual role as both an active agent and a sweetener in a cookie or other comestible unit. This renders the units very effective as a means for drug delivery for children and for simultaneously providing a reduced sugar snack.

The isomer myo-inositol—again the most prominent form of naturally occurring inositol—is a meso compound which has an optically inactive plane of symmetry through the molecule. Besides myo-inositol, the other naturally occurring (albeit uncommon) stereoisomers are scyllo-, muco-, D-chiro-, and neo-inositol. Other isomers are L-chiro-, allo-, epi-, and cis-inositol.

The structure of the most common natural form of inositol, myo-inositol, is shown below:

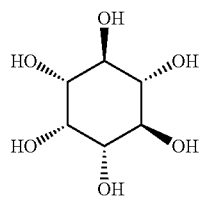 [SMILES: O[C@H]1[C@H](O)[C@@H](O)[C@H](O)[C@@H](O)[C@H]1O]

A preferred form of inositol for use according to some embodiments of the present invention is myo-inositol sold in powder form under the name FREEDA®. Unless otherwise stated in this specification, the tem "inositol" or "standard inositol" refers to myo-inositol having a potency substantially similar to that of the inositol powder referenced above, e.g., sold under the name FREEDA®, or other brands and dosage forms having substantially similar potencies. Therapeutically effective doses of inositol (e.g., in powder form) for patients with ASD may generally range from about 4,500 mg to about 32,400 mg per day and preferably from about 9,000 mg to about 32,400 mg per day and especially preferably from about 12,000 mg to about 32,400 mg per day, or optionally from about 12,000 mg to about 24,000 mg per day, or optionally from about 12,000 to about 18,000 mg per day. Optionally, a therapeutically effective dose of inositol is at least 9,000 mg.

Once daily administration of inositol within the foregoing dosage amounts is within the scope of the invention. However, twice daily or three times daily administration is preferred. For example, if a preferred daily dose of inositol for a given patient is 21,000 mg, it is preferred that the inositol be administered to the patient, e.g., 10,500 mg in the morning and 10,500 mg in the evening (twice daily dosing) or 7,000 in the morning, 7,000 around lunch time and 7,000 in the evening (three times daily dosing).

The above recited dosing of inositol may also be effective in treating one or more of the following symptoms, irrespective of whether such symptoms stem from a DSM-recognized psychiatric disorder or neurological disorder: anxiety, hypersensitivity, restricted areas of interest, repetitive behaviors, irritability and emotional lability. The above recited dosing of inositol may also be effective in providing a calming effect to a patient in need thereof. Optionally, in any embodiment, the patient experiences a therapeutic effect after two weeks of consistent inositol administration.

In treating ASD patients with inositol, the Applicant has discovered, among other things, the following noteworthy phenomena:

(1) Inositol may be safely administered, with only the minimal side effect of diarrhea, in doses that significantly exceed doses given to some non-ASD patients described in the literature.

(2) By and large, children (i.e., under age 18) as a population tend to tolerate higher doses of inositol than adults as a population, in terms of the side-effect of diarrhea. For example, as a population, children tend to respond well to about 9,000 mg or more of inositol twice a day, whereas adults tend to tolerate (but at the same time, only require) about half as much. A minority of patients, especially in the adult population, experience diarrhea with much lower doses of inositol. For example, the Applicant has treated patients for whom about 500 mg per day was the maximum dose that would avoid diarrhea, yet that dose was still therapeutically effective in those patients.

(3) The Applicant has found a correlation between the maximum effective dose of inositol in an ASD patient and the point at which the inositol induces diarrhea in the patient. In other words, once a patient experiences diarrhea from inositol, the point of diminishing returns has been reached, as it appears to the Applicant that increasing the inositol dose at that point will not further reduce symptoms to a clinically meaningful degree. While the Applicant would not recommend deliberately inducing diarrhea in a patient for ethical reasons, it is believed that the maximum effective dose of inositol for a given patient is immediately below an amount that induces diarrhea in the patient. The preferred therapeutically effective dose of inositol is the maximum effective dose, although the present invention may include doses of inositol that are therapeutically effective and below the maximum effective dose. While it is not practical to dose titrate patients on inositol by altering the hundreds or more likely thousands of milligram doses of inositol one milligram at a time, one may alter the dose by tens or more likely hundreds of milligrams at a time to determine the maximum effective dose of inositol. For example, in one aspect of the present invention, the maximum effective dose of inositol for a given patient is determined by providing an amount of inositol to the patient that induces diarrhea and then titrating down to a lower dose that does not induce diarrhea but is immediately below a dose which does induce diarrhea, wherein the maximum effective dose is the lower dose. A physician may titrate down, e.g., in increments of 5% or 10% of the amount of inositol that induces diarrhea in the patient. Optionally, the maximum effective dose is within 10% of the amount of inositol that induces diarrhea in the patient. In such an embodiment, for example, the maximum effective dose for a patient who experienced diarrhea at 18,000 mg of inositol per day may be immediately below 18,000 mg, including as low as 16,200 mg.

Even though these findings were based on administration to ASD patients, it is contemplated that the same general dosing guidelines can be used in treating one or more of the following symptoms, irrespective of whether such symptoms stem from a DSM-recognized psychiatric disorder or neurological disorder: anxiety, hypersensitivity, restricted areas of interest, repetitive behaviors, irritability and emotional lability. Likewise, it is contemplated that the same general dosing guidelines can be used to provide a calming effect to a patient.

While it is currently preferred that the inositol is administered within the nominal dosage ranges described above, it is contemplated that the potency of inositol may be increased such that it may be administered in lesser nominal amounts than described above with reference to standard inositol, but still provide therapeutically equivalent effectiveness within the scope of the present invention. For example, the Applicant contemplates that inositol could be effectively administered in two to three times lower doses than the nominal amounts described above according to the teachings of U.S. Pat. No. 8,557,792, the entirety of which is incorporated herein by reference. That patent discloses a vitamin B12 formulation and inositol is considered to be part of the vitamin B complex.

Preferably, in accordance with an aspect of the present invention, the inositol powder is mixed into comestible units, such as cookie dough, in predetermined amounts adapted to provide therapeutic doses of inositol to a patient through administration of a plurality of such units to the patient. These comestible units are discussed in greater detail, below.

Comestible Units Comprising Inositol

In one aspect, the present invention is directed to a method for reducing, to a clinically meaningful degree, one or more symptoms associated with ASD in a patient having ASD, e.g., part B of the DSM 5.0 definition of ASD and/or emotional lability/irritability. Alternatively, the present invention is directed to treating one or more of the following symptoms, irrespective of whether such symptoms stem from a DSM-recognized psychiatric disorder or neurological disorder: anxiety, hypersensitivity, restricted areas of interest, repetitive behaviors, irritability and emotional lability. In any case, the method comprises administering to the patient a therapeutically effective amount of inositol, wherein the therapeutically effective amount of inositol is from about 9,000 mg to about 32,400 mg per day. This may be achieved, e.g., through administering a plurality of comestible units comprising a predetermined amount of inositol to a patient.

The comestible unit is a solid or substantially solid food, as opposed to a drink. The comestible unit is preferably a baked good, candy or other food that is appealing to ASD or other patients, especially children, who are particularly sensitive to bad tastes and odors. Preferably, the comestible unit is a cookie or other small measured quantity of food that is not overly filling per unit. In this way, a patient may consume therapeutic doses of inositol by consuming a plurality of such units. Preferably, a comestible unit is packaged together with a plurality of other similarly sized units, wherein every unit contains substantially the same amount of inositol. In this way, a patient or caretaker does not need to premeasure inositol powder for each administration and mix the powder into a delivery liquid (e.g., juice) or semi-solid food (e.g., applesauce). The comestible units thus simplify administration of inositol and make taking the medicine an enjoyable experience for the patient.

Optionally, each comestible unit (e.g., cookie) includes predetermined amounts of from 1,000 to 7,000 mg of inositol, optionally from 1,500 to 6,000 mg of inositol, optionally from 2,000 to 5,500 mg of inositol, optionally from 2,000 to 4,500 mg of inositol, optionally from 2,000 to 3,000 mg of inositol, optionally from 2,500 to 4,500 mg of inositol, optionally from 2,500 to 3,500 mg of inositol, optionally from 3,000 to 4,500 mg of inositol, or optionally precisely or about (i.e., plus or minus 50 mg) any of the following amounts of inositol: 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,100 mg, 3,200 mg, 3,300 mg, 3,400 mg, 3,500 mg, 3,600 mg, 3,700 mg, 3,800 mg, 3,900 mg, 4,000 mg, 4,100 mg, 4,200 mg, 4,300 mg, 4,400 mg, 4,500 mg, 4,600 mg, 4,700 mg, 4,800 mg, 4,900 mg, 5,000 mg, 5,100 mg, 5,200 mg, 5,300 mg, 5,400 mg, or 5,500 mg.

Since inositol has a sweet taste, the foregoing exemplary amounts of inositol may be used to reduce or replace sugar in comestible units according to the present invention. For example, in one embodiment, the invention may be a cookie made from the following ingredients: unbleached flour, vegetable oil, a predetermined amount of inositol, (optionally) sugar, cocoa, eggs, water, honey, salt, leavening and vanilla, wherein the predetermined amount of inositol per cookie is optionally precisely or about (i.e., plus or minus 50 mg) any of the following: 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,100 mg, 3,200 mg, 3,300 mg, 3,400 mg, 3,500 mg, 3,600 mg, 3,700 mg, 3,800 mg, 3,900 mg, 4,000 mg, 4,100 mg, 4,200 mg, 4,300 mg, 4,400 mg, 4,500 mg, 4,600 mg, 4,700 mg, 4,800 mg, 4,900 mg, 5,000 mg, 5,100 mg, 5,200 mg, 5,300 mg, 5,400 mg, or 5,500 mg.

Preferably the comestible units are packaged with a plurality of other such units, with printed indicia on or in a package containing such units, communicating that the units and/or high doses of inositol may be effective in treating ASD or have been shown to be effective in treating ASD and/or one or more of the following symptoms: anxiety, hypersensitivity, restricted areas of interest, repetitive behaviors, irritability and emotional lability (irrespective of whether such symptoms stem from a DSM-recognized psychiatric disorder or neurological disorder) and/or for providing a calming effect (irrespective of specific symptomology or underlying condition). The package may also provide printed indicia stating that the comestibles, when consumed according to dosing described herein, may provide a therapeutic effect (e.g., the foregoing effects or treatment of symptoms) after two weeks of consistent administration to the patient. For example, a package of inositol-containing cookies may include indicia to any of the aforementioned effects. A package of inositol-containing comestible units may further include printed indicia communicating that the units and/or high doses of inositol may cause diarrhea and/or that the preferred amount of inositol for a given patient is to be provided in one unit less than the number of units daily that induce diarrhea in a given patient.

Aside from cookies, by way of example only, the inositol-containing comestible units may be brownies, pastries, doughnuts, graham crackers, candies, cakes, chocolates, cereal bars, pies, wafers, muffins, cupcakes, gummies and lollipops, or other sweet food units.

Optionally, in any embodiment, the inositol-containing comestible units are prepared in a cooking or baking process wherein the units are heated in an oven environment that is set at least 300° F. or higher for at least eight minutes. Optionally, the therapeutically effective amount of inositol is from 18,000 mg to 32,400 mg per day, the plurality of inositol-containing comestible units are cookies, wherein each cookie contains from 2,500 to 4,500 mg of inositol, the method comprising administering to the patient two to four cookies two or three times daily. Preferably, in this and other embodiments disclosed herein, the inositol in the plurality of inositol-containing comestible units does not have reduced efficacy in treating the patient due to the inositol being exposed to high temperatures during baking, compared to an identical dose of inositol administered in raw powder form.

Optionally, in any embodiment, the inositol-containing comestible units are lozenges, gummies or candies.

Combination Therapy

As discussed above, combination therapy is the subject of Applicant's earlier filed patent applications, including U.S. Pat. Pub. 2014/0309271 (the "'271 application"). In one embodiment, the inositol-containing comestible units of the present invention may be administered in combination with an alpha-2 adrenergic agonist in an extended release dosage form, to treat ASD, according to methods disclosed in the '271 application.

Measurement of Symptoms

It is within the ability of a psychiatrist of ordinary skill to assess each of the various symptoms and diagnostic criteria for ASD generally and for other symptoms associated with ASD (or symptoms unrelated to ASD) described herein, in a clinical setting, using his or her training and experience. Optionally, a psychiatrist may desire to measure these symptoms and criteria using a recognized quantitative scale in the field of ASD or psychiatry generally, optionally the Social Responsiveness Scale ("SRS"). The Social Responsiveness Scale (SRS) (Constantino, J. et al., J Dev Behav Pediatr, 21:2-11 (2000); Constantino, J. et al., J Autism Dev Disord., 3:427-433 (2003)) is a norm-referenced, 65-item report questionnaire developed to measure social behaviors, including social awareness, social information processing, reciprocal social communication, and social anxiety, in both clinical and non-clinical populations. It is designed for use with children ages 4 through 18. The SRS items measure symptoms in the domains of social awareness, social information processing, reciprocal social communication, social anxiety/avoidance, and stereotypic behavior/restricted interests. Each item is scored from 1 (not true) to 4 (almost always true). Scores are obtained for five treatment subscales: Social Awareness (e.g., "Is aware of what others are thinking or feeling"), Social Cognition (e.g., "Doesn't recognize when others are trying to take advantage of him or her"), Social Communication (e.g., "Avoids eye contact or has unusual eye contact"), Social Motivation (e.g., "Would rather be alone than with others"), and Autistic Mannerisms (e.g., "Has an unusually narrow range of interests").

Examples of Treatment for Patients

Aspects of the present invention are further explained by the following examples which should not be construed by way of limiting the scope of the present invention.

Example 1

Cookies are made to contain 2,700 mg of inositol power each (¾ tsp of FREEDA® brand inositol powder having a concentration of 900 mg per ¼ tsp). The inositol acts as a sweetener which allows reduction in sugar content of each cookie.

It is found that preferred dosing of these 2,700 mg inositol cookies is two to four cookies two or three times daily for ASD patients, titrated until a given ASD patient reaches his/her diarrhea threshold. It is found that these inositol-containing cookies at these doses are effective in treating symptoms of ASD, including part B of the DSM 5.0 definition of ASD and emotional liability/irritability.

Optionally, the cookies are taken in combination with therapeutically effective amounts of extended release clonidine (KAPVAY®) or extended release guanfacine (INTUNIV®).

Example 2

Cookies are made to contain 3,600 mg of inositol power each (1 tsp of FREEDA® brand inositol powder having a concentration of 900 mg per ¼ tsp). The inositol acts as a sweetener which allows reduction in sugar content of each cookie.

It is found that preferred dosing of these 3,600 mg inositol cookies is two to three cookies two times daily for ASD patients, titrated until a given ASD patient reaches his/her diarrhea threshold. It is found that these inositol-containing cookies at these doses are effective in treating symptoms of ASD, including part B of the DSM 5.0 definition of ASD and emotional lability/irritability.

Optionally, the cookies are taken in combination with therapeutically effective amounts of extended release clonidine (KAPVAY®) or extended release guanfacine (INTUNIV®).

Example 3

In a study, a group of 24 ASD patients are given the cookies of Example 2 above, according to the dosing guidelines described therein (i.e., titrated to each patient's diarrhea threshold). After three weeks, it is observed that 22 out of the 24 patients' ASD symptoms are alleviated, particularly in the domains of part B of the DSM 5.0 definition of ASD and emotional lability/irritability.

The 24 patients are then separated into two groups. Twelve of these patients continue on the same treatment as before. The other twelve are, without their knowledge, switched to cookies that appear and taste essentially identical to the inositol-containing cookies, except that these new cookies (the placebo cookies) contain no inositol. After two weeks, the treated group continues to respond as well as it had after the first three weeks of the study. However, the patients in the placebo group revert back to their pre-treatment symptomology, and in some cases worse than their pre-treatment symptomology.

This example shows how, in one aspect, the invention may provide an effective tool in a clinical trial to render a switch from inositol-containing cookies to placebo cookies imperceptible (in taste, appearance, texture, etc.) to a patient.

Example 4

Example 4 of the '271 application describes a retrospective study of medical charts of the Applicant's ASD patients who, in addition to having the core symptoms of ASD, also had symptoms associated with ASD (impulsivity, concentration deficit or attention deficit and emotional lability/irritability). That example presented data showing superior efficacy of Applicant's combination therapy in treating ASD compared to using either agent alone. The present example isolates the data from Example 4 of the '271 application relating to use of high doses of inositol as a monotherapy for ASD.

175 of these patients had initially received some form of medication (not treatment according to the present invention) or had been given psychotherapy without medication. Of these, 22% responded in some way to the medication and 17% responded in some way to psychotherapy alone. 77% of those on one or more of the following medications experienced adverse effects: stimulants, SSRI's, SNRI's, mood stabilizers, antipsychotics, benzodiazepines and immediate release alpha-2 agonists.

66 of the study patients were given high doses of inositol as a monotherapy. 62 of the 66 patients (94%) showed improvement in part B of the DSM 5.0 definition of ASD and the associated ASD symptom of emotional lability/irritability. 12% of inositol monotherapy patients experienced a minimal side effect of diarrhea, which was substantially resolved with dosage reduction.

While combination therapy was certainly shown to be superior, monotherapy using high doses of inositol was still shown to be effective in treating some symptoms in ASD.

Example 5

A study is conducted involving 28 patients who qualify for an ASD diagnosis. In a first phase, these patients are divided into two groups: a drug group (16 patients) that receives therapeutic amounts of inositol (average from 9,000 mg to 18,000 mg per day) in an oral powder dosage form for two weeks; and a placebo group (12 patients) that receives a confectionary sugar-based powdered placebo (intended to represent inositol) for two weeks. Neither group receives any other psychiatric drug during the two weeks of drug or placebo administration. After those two weeks, the progress of the patients in the two groups are measured according to the SRS. It is found that all 16 patients in the drug (inositol alone) group show clinically meaningful reduction in the restricted areas of interest and repetitive behaviors subscale of the SRS. However, none of the 12 patients in the placebo group show any measurable reduction in the restricted areas of interest and repetitive behaviors subscale of the SRS.

Example 6

The Applicant's preferred brand of inositol, FREEDA®, provides information on the bottle stating that the serving size for adults is 900 mg, that the bottle should be kept out of the reach of children, that the product should be stored at room temperature and that the product should not be exposed to excessive heat or moisture. Notwithstanding these statements, Applicant determined that approximately twenty times the specified serving size for adults is safe and effective for treating children having ASD or otherwise experiencing anxiety, hypersensitivity, restricted areas of interest, repetitive behaviors, irritability and emotional lability (irrespective of whether such symptoms are rooted in an underlying psychiatric disorder or neurological disorder). Applicant further found that these large doses of inositol surprisingly retained their efficacy when mixed into hot liquids or semi-solids (e.g., oatmeal).

Based on these findings and in view of difficulties associated with administering large amounts of inositol powder to children. Applicant worked with a cookie company to try to fit as much inositol in standard sized cookies as possible. Applicant set out to make the cookie retain a good taste and texture so as to render the presence of the inositol virtually unnoticeable to a child eating the cookie. Applicant and the company ultimately created a cookie (sold under the name CALMINTOL) that included 3,165 mg inositol per cookie. The CALMINTOL package states that there are three cookies per serving (i.e., 9,495 mg per serving). Applicant recommends two servings per day for patients in need thereof (e.g., approximately 20,000 mg daily, give or take).

It was found that these cookies treated ASD symptoms as well as other symptoms that may or may not be rooted in ASD or another underlying psychiatric or neurological condition. It is contemplated that these cookies are useful in treating a patient having one or more of the following symptoms: anxiety, hypersensitivity, restricted areas of interest, repetitive behaviors, irritability and emotional lability, or otherwise providing a calming effect to a patient in need thereof (irrespective of whether such symptoms stem from a DSM-recognized psychiatric disorder or neurological disorder).

The cookie company was initially skeptical about making this cookie because it is extremely unconventional in the food industry to incorporate such high pharmacological doses of active agents in foods, especially foods primarily intended for children. This skepticism is based on several factors. For one, while food may often be "fortified with" or naturally contain low levels of vitamins or minerals, food is not typically used as a delivery vehicle for pharmacological doses of active substances. For example, inositol is provided in infant formula in amounts less than 5 mg. per 5 fl. oz. serving. Moreover, the FREEDA® inositol bottle provides that the serving size for adults is 0.9 grams and the bottle prominently says, "Keep out of the reach of children." In addition, the bottle warns that the product should be stored at room temperature and should not be "expose[d] to excessive heat or moisture." Based on these factors, a skilled artisan would reasonably expect that the inositol dosing of the cookies is excessive for children and that the inositol's potency would be adversely affected by the extreme conditions to which it would be subject during the baking process. Nevertheless, it has been surprisingly found that the inositol in fact did not measurably lose efficacy in the baking process and that the CALMINTOL cookies successfully and safely treated symptoms in pediatric patients.

While the invention has been described in detail and with reference to specific examples thereof, it will be apparent to one skilled in the art that various changes and modifications can be made therein without departing from the spirit and scope thereof.

What is claimed is:

1. A method for treating a patient, the method comprising: administering to the patient a therapeutically effective amount of inositol, wherein the therapeutically effective amount of inositol is at least 12,000 mg per day and the therapeutically effective amount of inositol is cumulatively provided in a plurality of inositol-containing comestible units per day, wherein the inositol-containing comestible units are prepared in a cooking or baking process wherein the units are heated in an oven environment that is set at least 300° F. or higher for at least eight minutes, wherein each comestible unit comprises a predetermined amount of inositol, the predetermined amount of inositol being from 1,500 to 6,000 mg of inositol, wherein the method is effective in treating one or more symptoms, whether or not such symptoms are rooted in an underlying psychiatric disorder or neurological disorder, wherein the symptoms are selected from the group consisting of: anxiety, hypersensitivity, restricted areas of interest, repetitive behaviors, irritability and emotional lability.

2. The method of claim 1, wherein the predetermined amount of inositol is selected from an amount consisting of about: 1,500 mg, 1,600 mg, 1,700 mg, 1,800 mg, 1,900 mg, 2,000 mg, 2,100 mg, 2,200 mg, 2,300 mg, 2,400 mg, 2,500 mg, 2,600 mg, 2,700 mg, 2,800 mg, 2,900 mg, 3,000 mg, 3,100 mg, 3,200 mg, 3,300 mg, 3,400 mg, 3,500 mg, 3,600 mg, 3,700 mg, 3,800 mg, 3,900 mg, 4,000 mg, 4,100 mg, 4,200 mg, 4,300 mg, 4,400 mg, 4,500 mg, 4,600 mg, 4,700 mg, 4,800 mg, 4,900 mg, 5,000 mg, 5,100 mg, 5,200 mg, 5,300 mg, 5,400 mg, and 5,500.

3. The method of claim 1, wherein the predetermined amount of inositol is from 3,000 to 6,000 mg of inositol.

4. The method of claim 1, wherein the plurality of inositol-containing comestible units are selected from the group consisting of: cookies, brownies, pastries, doughnuts, graham crackers, cakes, chocolates, cereal bars, pies, wafers, muffins and cupcakes.

5. The method of claim 1, wherein the plurality of inositol-containing comestible units are cookies, wherein each cookie contains from 2,500 to 4,500 mg of inositol, the method comprising administering to the patient two to four cookies two or three times daily.

6. The method of claim 4, comprising administering to the patient two to four comestible units two or three times daily.

7. The method of claim 6, wherein each comestible unit contains from 2,500 to 4,500 mg of inositol.

8. The method of claim 1, wherein the therapeutically effective amount of inositol is up to 32,400 mg per day.

9. The method of claim 1, wherein the therapeutically effective amount of inositol is from 15,000 mg to 32,400 mg per day.

10. The method of claim 1, wherein the therapeutically effective amount of inositol is from 18,000 mg to 32,400 mg per day.

11. The method of claim 1, wherein the therapeutically effective amount of inositol is from 18,000 mg to 32,400 mg per day, the plurality of inositol-containing comestible units are cookies and each cookie contains from 2,500 to 4,500 mg of inositol, the method comprising administering to the patient two to four cookies two or three times daily.

12. The method of claim 11, wherein the method induces diarrhea in the patient and wherein the diarrhea is alleviated by reducing the amount of inositol administered to a maximum effective dose of inositol, the method providing a therapeutic effect which is not diminished at the maximum effective dose compared to a therapeutic effect the patient experienced when the method induced diarrhea in the patient.

13. The method of claim 1, wherein the inositol-containing comestible units are baked goods, wherein the inositol in the plurality of inositol-containing comestible units does not have reduced therapeutic potency due to the inositol being exposed to high temperatures during baking, compared to an identical dose of inositol administered in raw powder form.

14. The method of claim 1, wherein the inositol-containing comestible units are baked goods.

15. The method of claim 1, wherein the therapeutically effective amount of inositol is from 18,000 mg to 32,400 mg per day, the plurality of inositol-containing comestible units are cookies, wherein each cookie contains from 2,500 to 4,500 mg of inositol, the method comprising administering to the patient two to four cookies two or three times daily.

16. The method of claim 1, wherein the inositol in the plurality of inositol-containing comestible units does not have reduced therapeutic potency due to the inositol being exposed to high temperatures during the cooking or baking process, compared to an identical dose of inositol administered in raw powder form.

17. The method of claim 1, wherein the inositol-containing comestible units are gummies or candies.

* * * * *